United States Patent [19]

Kaplan

[11] Patent Number: 4,626,541

[45] Date of Patent: Dec. 2, 1986

[54] WATER SOLUBLE SALT COMPOSITION OF M-AMSA

[75] Inventor: Murray A. Kaplan, Syracuse, N.Y.

[73] Assignee: Bristol-Myers Company, New York, N.Y.

[21] Appl. No.: 775,478

[22] Filed: Sep. 12, 1985

[51] Int. Cl.$^4$ ............................................. A61K 31/44
[52] U.S. Cl. ................................................. 514/297
[58] Field of Search ......................................... 514/297

[56] References Cited

U.S. PATENT DOCUMENTS 4,335,244  6/1982  Kaplan et al. ........................ 546/106
4,360,523  11/1982  Kaplan et al. ....................... 546/106
4,425,348  1/1984  Kaplan et al. ........................ 546/106

FOREIGN PATENT DOCUMENTS 42553  12/1981  European Pat. Off. .

*Primary Examiner*—Stanley J. Friedman
*Attorney, Agent, or Firm*—David M. Morse

[57] ABSTRACT

This invention relates to novel compositions of the antitumor agent [4'-9-(acridinylamino) methanesulfon-m-anisidide] (m-AMSA). The lactate salts of the m-AMSA composition in admixture with pyroglutamic acid provide a highly stable, highly water soluble product.

13 Claims, No Drawings

WATER SOLUBLE SALT COMPOSITION OF M-AMSA

BACKGROUND OF THE INVENTION

1. Field of the Invention

The novel compositions of the present invention possess the advantageous pharmacological properties of the known free base compound and in addition have unexpectedly high water-solubility, thus allowing preparation of useful dosage forms for intravenous administration

2. Description of the Prior Art

The acridine derivative m-AMSA [4'9-(acridinylamino)methanesulfon-m-anisidide] has been reported by Cain, et al. in Europ. J. Cancer 10:539–549 (1974) to possess significant antitumor activity in animal tumor systems.

When an antitumor agent such as m-AMSA is employed for pharmaceutical use, it is recognized that solubility of the agent is often the controlling factor in determining route of administration and dosage forms. For instance, a water-soluble substance can be generally administered intravenously whereas a water-insoluble material is limited to other forms of parenteral administration such as intramuscular and subcutaneous. A therapeutic agent having water solubility also facilitates preparation of oral and non-intravenous parenteral dosage forms. Thus, it is decidedly advantageous if a therapeutic agent is water-soluble, particularly when one considers that the most direct route for achieving therapeutic blood levels of a drug is by intravenous administration.

The free-base form of m-AMSA has very limited solubility in water and thus cannot be used as a dosage form for intravenous administration. Attempts have been made to prepare acid addition salts to overcome this solubility problem, but the reported monohydrochloride and monomethanesulfonate salts also proved insufficiently water-soluble.

The m-AMSA formulation presently in clinical use consists of two sterile liquids combined just prior to use. A solution of m-AMSA in anhydrous N,N-dimethylacetamide is contained in an ampule. A separate vial contains an aqueous L(+)-lactic acid solution for use as a diluent. When mixed, the resulting m-AMSA solution is administered by i.v. infusion.

While the present clinical formulation provides an intravenous dosage form, it suffers from several disadvantages. In addition to the obvious difficulties in preparing and administering the dosage form, it contains dimethylacetamide as a vehicle. Dimethylacetamide has been reported to show various toxic symptoms in animals and may thus prove to be unacceptable or undesirale as a pharmaceutical vehicle.

It is accordingly an object of the present invention to provide water-soluble, stable, therapeutically acceptable forms of m-AMSA which can be administered intravenously (as well as by other routes) and which do not contain or require dimethylacetamide as a pharmaceutical vehicle. This object as well as other features and advantages of the invention will be readily apparent to those skilled in the art from the disclosure set out below.

The pyroglutamic acid (L and D,L-2-pyrrolidinone-5-carboxylic acid) used in admixture with the salts of the present invention or as a component of the compositions of the present invention has been reported in U.S. Pat. No. 3,920,814 to potentiate the instrinsic activity and blood levels of certain antibiotics such as penicillin G, penicillin V, ampicillin, cephalothin, gentamycin, tetracycline, etc. That patent also notes that pyroglutamic acid has been reported useful as a medicament for its good psychonormalizing, psychotonic, mood elevating and antitoxic action. Various other patent and literature references disclose pyroglutamate salts including, for example, Boll.Chim. Farm 116 (12): 735–743, 1977 (D,L-pyroglutamate salt of L(+)-arginine), Arzneim.Forsch. 27(8): 1553–1557, 1977 (D,L-pyroglutamate salt of L(+)-arginine), Japanese Published Patent Application No. 50/135,212 (D,L-2-pyrrolidinone-5-carboxylic acid triethanolamine salt as a component in pruritis treatment ointment), Japanese Patent No. 74/27,643 (triethanolammonium D,L-pyroglutamate as an ingredient in shampoo composition), U.S. Pat. No. 3,899,585 (pyroglutamic acid salts of amino acid higher alkyl esters as fungicidal and bactericidal agents; see also U.S. Pat. No. 3,821,403), U.S. Pat. No. 3,947,589 (pyroglutamic acid salts of N-higher aliphatic acyl amino acids for use as fungicidal compositions), Japanese patent No. 74/14,630 (D,L-pyroglutamic acid salts of amino acid alkyl esters for use as fungicides), U.K. Pat. No. 1,352,420 (discloses N-cocoyl-L(+)-arginine ethyl ester D,L-2-pyrrolidinone carboxylate as an antimicrobial or germicidal agent; see also West German Published Patent Application No. 2,131,404, Japanese Patent No. 76/22,055, Japanese Patent No. 76/5413, Oyo Yakuri 11 (6):945–953, 1976, Yukagaku 25 (7): 404–408, 1976, Mem. Tokyo Univ. Agric 20, 51–73, 1978, Japanese Patent No. 78/118,516 and Nippon Nogei Kagaku Kaishi 52 (3): 117–121, 1978.

SUMMARY OF THE INVENTION

The present invention provides stable, solid, water-soluble compositions for reconstitution with water or an aqueous vehicle as stable solutions of m-AMSA, said compositions comprising a mixture of an m-AMSA lactate salt and pyroglutamic acid, the molar ratio of the pyroglutamic acid to m-AMSA being from about 1:1 to about 2:1.

DETAILED DESCRIPTION

Many conventional pharmaceutically acceptable acid addition salts of m-AMSA are only slightly soluble in water and are thus unsuited for preparation of aqueous intravenous solutions. This is evident from literature references to the hydrochloride and methanesulfonate salts as well as from solubility tests carried out by the present inventors on salts such as the levulinate, citrate and lactobionate. Those lactate salts which are soluble at concentrations of 5 mg/ml can result in solutions which tend to form precipitates under extended storage at 24° C.

An investigation of the solubility properties of the crystalline L(+)-monolactate salt of m-AMSA indicates that it can precipitate from aqueous solution of greater than 2.5 mg/ml. While it has heretofore been assumed that aqueous solutions of m-AMSA lactate salts were physically stable at concentrations of 5 mg/ml or more of a true solution of m-AMSA, it has now been found that solutions of such salts under certain adverse field conditions could be latently physically unstable, even at room temperature and will form precipitates at greater than 2.5 mg/ml which could interfere with the administration of the m-AMSA in an effective dosage form.

It has been recently and unexpectedly found that an m-AMSA L(+)-lactate monohydrate salt crystallized out of aqueous solution possesses an aqueous solubility of about 2.5 mg/ml, with excellent reconstitution rates and the stability necessary for use as an intravenous drug.

The m-AMSA L(+) lactate salts effectively eliminate the stability problems encountered at concentrations greater than 2.5 mg/ml. While such solubility is adequate for most purposes, it has now been discovered that higher concentrations of a stable solution may be obtained when 1 to 2 moles of L or D,L pyroglutamic acid is added per mole of lactic acid used in the preparation of the m-AMSA lactate dosage form.

Pyroglutamic acid may be obtained in the optically active D and L forms or as the optically inactive D,L-form. Of the various forms of pyroglutamic acid employed, the L(+) form appears to be most advantageous as an m-AMSA dosage form. Most preferably, the L-acid is employed because of the higher concentration obtained in the m-AMSA salt mixture.

The above described solid compositions may be employed in the form of either a dry-fill (mixture of dry components) or a lyophilized product. The solid dosage form of the L-isomer may be conveniently and rapidly reconstituted with water or a sterile aqueous vehicle to provide a maximum of 5-7.5 mg/ml true solution of m-AMSA having excellent physical and chemical stability characteristics. However, in addition to the L(+) and D,L-forms of pyroglutamic acid, it is contemplated that the D form may also be used.

Preparation of the water-soluble compositions of the present invention as a dry-fill mixture may be accomplished by simply mixing the appropriate starting materials in the proper proportions. Thus, the composition containing m-AMSA-lactate salt and pyroglutamic acid is prepared by mixing m-AMSA, L(+)-lactate and D,L or L-pyroglutamic acid in a ratio of about 1 to 2 moles of D,L or L-pyroglutamic acid per mole of lactic acid present. A preferred embodiment comprises a mixture of about 1 to 2 moles of D,L or L-pyroglutamic acid per mole of L(+)-lactic acid. As there is a possibility of precipitation occuring if the lactic acid is added to the m-AMSA at levels which yield concentrations greater than 2.5 mg/ml of m-AMSA lactate, it is preferred that the pyroglutamic acid be added to the m-AMSA slurry first. The resulting mixture upon lyophilization appears to yield the L(+)-lactate salt of m-AMSA stabilized or buffered with one mole equivalent of D,L or L-pyroglutamic acid.

Preparation of the water-soluble compositions as a lyophilized mixture may be accomplished by subjecting an aqueous solution of the appropriate starting materials in the proper proportions to a standard lyophilization process. Thus, the lyophilized m-AMSA lactate salt is prepared by reacting an aqueous solution of m-AMSA and either L(+), D(−)- or D,L lactic acid in a ratio of from about 0.1 to 1 mole of lactic acid per mole of m-AMSA base in the presence of 2 to 1 mole of D,L or L-pyroglutamic acid and then lyophilizing said aqueous solution to obtain the desired solid composition. Before the lyophilization step, the aqueous solution is preferably filtered to remove any insoluble impurities. Also, conventional excipients such as mannitol may be added to facilitate bulking and dissolution of the lyophilized product. Lyophilization may be carried out in conventional laboratory or industrial lyophilizers according to methods well-known to those skilled in the art. Illustrative lyophilization parameters are as follows:

precooling shelves at −20° C.;
  freezing at −50° C. for 4 hours;
  sublimation at −40° C. to +25° C. with a 10 millitorr vacuum for 38 hours; and
  drying at 30° C. under vacuum for 38 hours.

For preparation of unit dosage forms of the present compositions, the m-AMSA base may be used in any therapeutically effective dose. In the treatment of mammalian tumors, the salts and compositions of the present invention may be administered either orally or parenterally, but preferably in dosages (adjusted for the amount of the m-AMSA base) and according to regimens previously disclosed in the literature. A suggested dosage range of m-AMSA base in a unit dosage form is from about 20 to 100 milligrams.

The dry-fill and lyophilized compositions provided by the present invention exhibit substantially the same pharmacological properties as the prior art m-AMSA forms. Because of their water-solubility, however, they may be used to prepare dosage forms for intravenous administration which do not contain an undesirable pharmaceutical vehicle such as dimethylacetamide. Furthermore, because of their unusually good stability in solution the compositions may be used to prepare a multiple dose dry-fill or lyophilized product for reconstitution with sterile water or sterile aqueous vehicle as a parenteral dosage form.

The compositions of the present invention may be used to prepare oral or non-intravenous parenteral dosage forms as well as the preferred intravenous injectable product. The compositions have acceptable stability, both in solid form and in aqueous solution, to permit administration of an effective dose of m-AMSA in a relatively small volume of parenteral solution.

The compositions of the present invention may be administered either orally or parenterally, but preferable parenterally, in dosages (adjusted for amount of m-AMSA activity) and according to regimens previously disclosed in the literature. A particularly preferred dosage form is a reconstituted aqueous solution having 5 mg/ml of m-AMSA activity.

The dry-fills or lyophilized products may be either (a) m-AMSA free base plus 2 mole equivalents of L or D,L-pyroglutamic acid or (b) m-AMSA-L(+)-lactate or lactate monohydrate plus one mole equivalent of L or D,L-pyroglutamic acid.

In the above formulations, a mixture of m-AMSA-L(+)-lactate and 1 mole equivalent of D,L-pyroglutamic acid will provide a 5 mg/ml m-AMSA solution which will not precipitate. The use of L-pyroglutamic acid in place of D,L-pyroglutamic acid will provide a 5 to 7.5 mg/ml solution which will not precipitate.

A mixture of m-AMSA free-base and 2-molar equivalents of D,L-pyroglutamic acid will not precipitate at 5 to 7.5 mg/ml.

A mixture of m-ASMA free-base and 2 molar equivalents of L-pyroglutamic acid will not precipitate at 7.5 mg/ml of m-AMSA activity.

A particularly desirable feature of the present invention is that the remaining lyophilized cake, demonstrates no observable melting or shrinkage for as long as four months at temperatures of 45° to 55° C. A lyophilized m-AMSA lactate formulation containing one mole of L(+) lactic acid in excess under the same temperature conditions melts or shrinks significantly within 24 hours at 45° to 55° C.

The melting or shrinking creates a more dense product and may decrease the rate at which the lyophilized product can be reconstituted. The lyophilized composition of the present invention can provide aqueous solutions of 5–7.5 mg/ml in approximately one-3 minutes with moderate to rapid hand shaking.

The solutions containing 1 or 2 mole equivalents of L-pyroglutamic acid are stable for at least one year at 23°–25° C. with less than 10% activity loss and show no precipitation during such time. In addition, unlike m-AMSA lactate salt formulations which contain 1 mole of L(+) lactic acid in excess and tend to lose lactic acid during lyophilization, there is no apparent loss of lactic acid during lyophilization of the present compositions.

The following examples are given in illustration of, but not in limitation of, the present invention.

EXAMPLE 1

The m-AMSA-L(+)-lactate-pyroglutamate dosage forms of the present invention was prepared by the following procedure:

Ten grams of m-AMSA base was slurried, at 23°–25° C., in 175 ml of Sterile Water for Injection, U.S.P.

To the slurry was added 3.281 grams (1 molar equivalent) of L or D,L-pyroglutamic acid over a period of 3 minutes. The resulting solution had a pH of 3.5 to 4.0 and was moderately stirred for 5 minutes at 20°–25° C. To the resulting solution, 2.29 g (1 molar equivalent) of L(+) lactic acid was gradually added, while stirring was continued over 3 minutes to disperse all components. The volume was then brought up to 200 ml with Water for Injection, U.S.P. and stirred for an additional 0.5 hours. The resulting solution contained 5 mg/ml of m-AMSA activity. A pH 3.8 solution or near solution was obtained.

The solution was passed under a nitrogen atmosphere through a 0.22 micron pore size membrane filter using aseptic technique and the filtrate collected in a suitable sterile container.

Ten ml of filtrate at an activity of 5 mg/ml of m-AMSA was placed in 17.5 cc sterile flint glass vials and frozen at −40° C. in a sterile lyophilizer. The filtrate was lyophilized at a shelf temperature of 24°–27° C. to completion of the sublimation cycle. The vacuum was released to dry, sterile nitrogen and the vials sealed with rubber closures and aluminum shells.

EXAMPLE 2

A quantity, 12.74 grams of m-AMSA L(+)-lactate monohydrate crystals (10 g of m-AMSA activity) are dissolved in sterile, purified water qs. to 200 ml with 1 mole of L or D,L-pyroglutamic acid (3.281 g). The resulting 5 mg/ml of m-AMSA activity solution is filtered through a 0.22 micron membrane filter for clarification. The filtrate is then added to suitable flint glass vials (e.g. 5.0 ml. solution per vial). The vials are then partially stoppered and subjected to lyophylization at the following parameters:

prefreezing at −55° C.;
freezing at −50° C. for 2 hours;
sublimation at −40° C. to +25° C. for about 68 hours at a pressure of 10 millitorr; and
drying at +30° C. under vacuum for about 48 hours.

The vials are then stoppered under vacuum or nitrogen and sealed. The lyophilized composition can be reconstituted with water to give (at 25° C.) at least a 5.0 mg/ml highly stable solution of m-AMSA activity. Reconstitution time is about 1 to 3 minutes. Lyophilized vials were found to have acceptable stability upon reconstitution after 3 months storage at 56° C.

EXAMPLE 3

Five hundred mg of m-AMSA free base was added to 99.5 ml of Sterile Water for Injection U.S.P. and stirred to form a slurry. To the slurry was then added 165 mg of L or D,L pyroglutamic acid, with stirring. To the resultant near solution was then added 114 mg of L(+)-lactic acid. The solution was stirred to incorporate the lactic acid and then passed through a Millex-HA filter to remove a small amount of insolubles.

Four ml of the resulting 5 mg/ml of m-AMSA activity solution was placed into 8.5 cc flint glass vials and lyophilized for 48 hours under the conditions described in Example 1.

EXAMPLE 4

Seven and one half grams of m-AMSA base was slurried at 23°–25° C., in 900 ml of sterile water for injection, U.S.P.

To the slurry was added 2.46 g of L or D,L-pyroglutamic acid (1-mole equivalent) over a period of 3 minutes. The resulting near solution had a pH of 3.5 to 4.0 and was moderately stirred for 10 minutes. To the resulting near solution, 1.72 g of L(+)-lactic acid (1 mole equivalent) was gradually added over 3 minutes to disperse all components. The volume was then adjusted to 1 L and the solution stirred for an additional 10 hours. The resulting solution contained 7.5 mg/ml of m-AMSA activity.

Ten cc of filtrate of an activity of 7.5 mg/ml of m-AMSA was placed in 17.5 cc sterile flint glass vials and frozen at −40° C. in a lyophilizer. The filtrate was lyophilized at a shelf temperature of 24°–27° C. to completion of the sublimation cycle. The vacuum was released to dry, sterile nitrogen and the vials sealed with rubber closures and aluminium shells.

EXAMPLE 5

One mole m-AMSA-L(+)-lactate plus one mole equivalent of L-pyroglutamic acid was combined to form a dry fill. The product was subjected to accelerated storage with the following results:

| Time | % loss |
| --- | --- |
| 1 week (70° C.) | 3.4 |
| 2 weeks (70° C.) | 5.5 |
| 6 weeks (56° C.) | 3.8 |
| 6 weeks (45° C.) | 1.9 |

The foregoing samples all reconstituted at 5 mg/ml in under 2 minutes. Based on the above data it is predicted that the compositions should lose less than 10% activity when stored up to three years at 24° C.

What is claimed is:

1. The lactate salt of m-AMSA in admixture with pyroglutamic acid, prepared from at least 2 moles of acid, the molar ratio of pyroglutamic acid to lactic acid used to prepare the salt being from about 0.1 to 1 mole lactic acid to 2 to 1 mole of pyroglutamic acid.

2. A composition according to claim 1 wherein the pyroglutamic acid is L-pyroglutamic acid and the molar ratio of L-pyroglutamic acid to lactic acid is from about 1:1 to 2:1.

3. A composition according to claim 1 wherein the pyroglutamic acid is D, pyroglutamic acid and the molar ratio of D, pyroglutamic acid to lactic acid is from about 1:1 to 2:1.

4. A composition according to claim 1 wherein the pyroglutamic acid is D,L pyroglutamic acid and the molar ratio of D,L pyroglutamic acid to lactic acid is from about 1:1 to 2:1.

5. A composition according to claim 1, 2, 3 or 4 wherein said lactic acid is L(+) lactic acid.

6. A composition according to claim 1, 2, 3 or 4 wherein said lactic acid is D(−) lactic acid.

7. The composition according to claim 1, 2, 3 or 4 wherein said lactic acid is D,L-lactic acid.

8. A stable, solid, water-soluble pharmaceutical composition in dosage form suitable for reconstitution with water or aqueous vehicle to provide a stable aqueous solution of m-AMSA, said composition consisting of a mixture of about 20 to 200 milligrams of an m-AMSA lactate salt with about 1 to 2 molar equivalents of pyroglutamic acid.

9. A composition according to claim 8 wherein said pyroglutamic acid is L-pyroglutamic acid.

10. A composition according to claim 8 wherein said pyroglutamic acid is D,L-pyroglutamic acid.

11. A composition according to either claim 9 or 10 wherein said lactate salt is derived from L(+) lactic acid.

12. A composition according to either claim 9 or 10 wherein said lactate salt is derived from D(−) lactic acid.

13. A composition according to either claim 9 or 10 wherein said lactate salt is derived from D,L-lactic acid.

* * * * *